United States Patent
Degischer et al.

(10) Patent No.: US 6,521,564 B2
(45) Date of Patent: Feb. 18, 2003

(54) MODIFICATION OF A HYDROGENATION CATALYST

(75) Inventors: Oliver Gerald Degischer, Zürich (CH); Felix Roessler, Kaiseraugst (CH)

(73) Assignee: Roche Vitamins, Inc., Parsippany, NJ (US)

( * ) Notice: Subject to any disclaimer, the term of this patent is extended or adjusted under 35 U.S.C. 154(b) by 0 days.

(21) Appl. No.: 09/726,877

(22) Filed: Nov. 30, 2000

(65) Prior Publication Data

US 2001/0004672 A1 Jun. 21, 2001

(30) Foreign Application Priority Data

Dec. 16, 1999 (EP) ............................................. 99125081
Sep. 28, 2000 (EP) ............................................. 00121068

(51) Int. Cl.$^7$ ........................... B01J 25/04; B01J 25/02; B01J 25/00; C07C 207/48
(52) U.S. Cl. ........................... 502/301; 502/20; 502/33; 502/34; 502/172; 502/501; 502/514; 502/523; 564/413; 564/415; 564/487; 564/448; 564/490
(58) Field of Search ................................ 502/501, 514, 502/523, 301, 20, 33, 34, 172; 564/413, 415, 487, 490, 448

(56) References Cited

U.S. PATENT DOCUMENTS 3,953,367 A 4/1976 Hoffmann et al. ........... 253/463
5,296,628 A 3/1994 Sanchez

FOREIGN PATENT DOCUMENTS

GB 1 206 981 9/1970

OTHER PUBLICATIONS

Derwent English language abstract of JP 53008288 (1978).
English translation of JP 2937083 (1999).
Besson, et al., "Catalytic hydrogenation of valeronitrile over Raney nickel. Part 1: Influence of reaction parameters on activity and selectivity," *Bull Soc Chim Fr*, vol. 127, pp. 5–12 (1990).

*Primary Examiner*—Brian Davis
(74) *Attorney, Agent, or Firm*—Bryan Cave LLP

(57) ABSTRACT

A process for the modification of a hydrogenation catalyst of the Raney nickel, Raney cobalt, nickel-on-carrier or cobalt-on-carrier type, which process includes treating the hydrogenation catalyst at temperatures of about 0° C. to about 120° C. with carbon monoxide, carbon dioxide, formaldehyde, a lower aliphatic aldehyde, an aromatic aldehyde, an aliphatic ketone, an aromatic ketone, a mixed aliphatic/aromatic ketone, glyoxal, pyruvaldehyde or glyoxylic acid as the modification agent in a liquid dispersion medium consisting of water or an organic solvent for a duration of about 15 minutes to about 24 hours. When the thus-modified catalyst is used in the hydrogenation of a nitrile to the corresponding amine, the selectivity is increased, and significantly favors the amount of the primary amine vis-à-vis the undesired secondary amine in the hydrogenation product as compared to when the corresponding unmodified catalyst is employed. The present invention concerns, in a second aspect, a process for the hydrogenation of a nitrile to the corresponding primary amine using a thus-modified catalyst.

19 Claims, No Drawings

MODIFICATION OF A HYDROGENATION CATALYST

FIELD OF THE INVENTION

The present invention is a process for the modification of a hydrogenation catalyst of the Raney nickel, Raney cobalt, nickel-on-carrier, or cobalt-on-carrier type.

SUMMARY OF THE INVENTION

As a consequence of the process, in which such a catalyst is treated with carbon monoxide, carbon dioxide, formaldehyde, a lower aliphatic aldehyde, an aromatic aldehyde, an aliphatic ketone, an aromatic ketone, a mixed aliphatic/aromatic ketone, glyoxal, pyruvaldehyde or glyoxylic acid, when the thus-modified catalyst is used in the hydrogenation of a nitrile to the corresponding amine the selectivity is increased. The increased selectivity favors significantly the amount of the primary amine vis-à-vis the undesired secondary amine in the hydrogenation product compared with the case when the corresponding unmodified catalyst is employed. The mode of the modification and the increased selectivity resulting therefrom are surprising. Accordingly, the present invention concerns, in a second aspect, a process for the hydrogenation of a nitrile to the corresponding primary amine using a thus-modified catalyst.

One embodiment of the invention is a process for modifying a hydrogenation catalyst of a Raney nickel, Raney cobalt, nickel-on-carrier or cobalt-on-carrier type. This process includes providing a hydrogenation catalyst of the Raney nickel, Raney cobalt, nickel-on-carrier, or cobalt-on-carrier type; and treating the hydrogenation catalyst at temperatures of about 0° C. to about 120° C. with a modification agent selected from the group consisting of carbon monoxide, carbon dioxide, formaldehyde, a lower aliphatic aldehyde, an aromatic aldehyde, an aliphatic ketone, an aromatic ketone, a mixed aliphatic/aromatic ketone, glyoxal, pyruvaldehyde, and glyoxylic acid in a liquid dispersion medium consisting of water or an organic solvent for about 15 minutes to about 24 hours.

Another embodiment of the invention is a process for the catalytic hydrogenation of a nitrile to its corresponding primary amine. This process includes providing a modified hydrogenation catalyst formed by treating a hydrogenation catalyst selected from the group consisting of a Raney nickel, Raney cobalt, nickel-on-carrier, and cobalt-on-carrier type catalyst at temperatures of about 0° C. to about 120° C. with a modification agent selected from the group consisting of carbon monoxide, carbon dioxide, formaldehyde, a lower aliphatic aldehyde, an aromatic aldehyde, an aliphatic ketone, an aromatic ketone, a mixed aliphatic/aromatic ketone, glyoxal, pyruvaldehyde, and glyoxylic acid in a liquid dispersion medium consisting of water or an organic solvent for a duration of about 15 minutes to about 24 hours; and contacting a nitrile with the modified hydrogenation catalyst to catalyze the reaction of the nitrile to its corresponding primary amine.

DETAILED DESCRIPTION OF THE INVENTION

The process in accordance with the invention for the modification of a hydrogenation catalyst of the Raney nickel, Raney cobalt, nickel-on-carrier or cobalt-on-carrier type includes treating the hydrogenation catalyst at temperatures of about 0° C. to about 120° C. with carbon monoxide, carbon dioxide, formaldehyde, a lower aliphatic aldehyde, an aromatic aldehyde, an aliphatic ketone, an aromatic ketone, a mixed aliphatic/aromatic ketone, glyoxal, pyruvaldehyde, or glyoxylic acid as the modification agent in a liquid dispersion medium consisting of water or an organic solvent for about 15 minutes to about 24 hours.

When the modification agent is formaldehyde, it can also be used in the form of metaldehyde or paraformaldehyde. Preferably, formaldehyde is used in the form of its aqueous solution, i.e. as formalin, in which case water then forms at least part of the liquid dispersion medium.

The "lower aliphatic aldehyde" which can be used as the modification agent in the present invention is preferably an aldehyde of the formula $R^1CHO$ in which $R^1$ is an alkyl group with 1 to 5 carbon atoms optionally substituted with hydroxy. The alkyl group can be straight-chained or branched depending on the number of carbon atoms. In the case where the alkyl group is substituted with hydroxy, one or more hydroxy substituents can be present. Preferably, acetaldehyde is used as such a modification agent.

The "aromatic aldehyde" which can be used as the modification agent in the present invention is especially an aldehyde of the formula $R^2CHO$ in which $R^2$ is an aryl or heteroaryl group. The term "aryl" as used herein embraces not only the usual unsubstituted aryl groups, i.e. phenyl and naphthyl, but also the corresponding substituted phenyl and naphthyl groups. The substituents may be, for example, halogen atoms and $C_{1-4}$-alkyl, hydroxy, $C_{1-4}$-alkoxy, amino, carbamoyl, and phenyl groups; in each case one or more substituents can be present. Fluorine, chlorine, bromine, or iodine is to be understood under the term "halogen." An alkyl or alkoxy group can be straight-chain or branched depending on the number of carbon atoms. In the case of multiple substituents the substituents may be the same or different. Normally, not more than 5 (for phenyl) or 7 (for naphthyl) halogen atoms, 3 alkyl groups, 2 hydroxy groups, 3 alkoxy groups, 2 amino groups, 2 carbamoyl groups, or one phenyl group may be present as a substituent. The term "heteroaryl" as used herein embraces heteroaryl groups which have one or more hetero atoms in the ring, such as nitrogen, oxygen, and/or sulphur atoms; pyridyl and pyrimidinyl are examples of such heteroaryl groups. Preferably, benzaldehyde or anisaldehyde is used as the aromatic aldehyde in the role of the modification agent.

The "aliphatic, aromatic or mixed aliphatic/aromatic ketone" which can be used as the modification agent in the present invention is preferably a ketone of the formula $R^3COR^4$ in which $R^3$ and $R^4$ each independently signify an alkyl, aryl, or heteroaryl group. The term "alkyl," "aryl," or "heteroaryl" as used herein are to be understood as above in connection with the definitions of $R^1$ and $R^2$. Preferably, acetone is used as such a modification agent.

In one embodiment of the invention carbon monoxide, formaldehyde or a lower aliphatic aldehyde is used as the modification agent.

The hydrogenation catalysts of the Raney nickel and Raney cobalt type which can be modified in the modification process in accordance with the invention are well known to a person skilled in the art and are readily obtainable commercially. The same applies to the catalysts of the nickel-on-carrier and cobalt-on-carrier type which likewise can be modified in the process. The carrier in these two cases may be, for example, silica, titanium oxide, aluminum oxide, kieselguhr, or active carbon.

Suitable organic solvents in which, in addition to water, the modification may be carried out include aliphatic hydrocarbons (e.g. pentane and hexane), aromatic hydrocarbons (e.g. benzene and toluene), alkanols (e.g. methanol, ethanol, and propanol), aliphatic and cyclic ethers (e.g. diethyl ether and, respectively, tetrahydrofuran, and dioxan), as well as heteroaromatics (e.g. pyridine). The dispersion medium can consist of water alone or of a single organic solvent or of two or more of such liquids. For example, an aqueous alkanol, e.g. aqueous ethanol, can be used as the liquid dispersion medium. In general, the process is carried out by dispersing the hydrogenation catalyst in water and/or such an organic solvent, because a dissolution of the catalyst does not take place due to its nature. On the other hand, the modification agent must at least partially dissolve in the dispersion medium, as will be explained in more detail below.

Based on the amount of hydrogenation catalyst to be modified, the amount of modification agent which is employed is as follows in the different cases:

| Modification Agent | Conveniently | Preferably |
|---|---|---|
| Carbon monoxide | 0.5–5 weight percent (wt. %) | 1–2 wt. % |
| Carbon dioxide | 1–30 wt. % | 5–15 wt. % |
| Formaldehyde, glyoxal, pyruvaldehyde, glyoxylic acid | 0.25–50 wt. % | 1–15 wt. % |
| Lower aliphatic aldehyde | 0.25–50 wt. % | 1–15 wt. % |
| Aromatic aldehyde | 0.25–50 wt. % | 1–15 wt. % |
| Aliphatic, aromatic or mixed aliphatic/aromatic ketone | 0.25–50 wt. % | 5–20 wt. % |

The amount of dispersion medium employed must be enough to disperse the hydrogenation catalyst so that the modification agent can act on the catalyst efficiently. The amount to be used depends on many factors, such as, for example, the design of the reactor and the rotation speed of a stirrer which is used, and can be readily established by a person skilled in the art by appropriate experimentation.

The temperature range in which the modification process in accordance with the invention is carried out is from about 0° C. to about 120° C. Preferably, the process is carried out at room temperature.

Depending on the modification agent and liquid dispersion medium used, on the amount of modification agent employed, as well as on the temperature at which the modification process is carried out, the modification agent can exert its effect in completely dissolved or partially dissolved form. For example, formaldehyde is usually employed in dissolved form, namely in an aqueous solution (as formalin), whereas paraformaldehyde is preferably employed in an almost undissolved (solid) form. During the modification process, the modification agent must be dispersed in the dispersion medium as homogeneously as possible (usually by adequate intermixing); this is especially important when the modification agent, such as, for example, carbon monoxide or paraformaldehyde, has a poor or only limited solubility in the dispersion medium. For this purpose stirring or shaking is preferably performed during the modification process in order to promote homogeneous distribution.

Furthermore, it is advantageous to avoid as far as possible contact of the hydrogenation catalyst with oxygen by the use of an inert gas, e.g. nitrogen or argon. In this manner, undesired deactivation of the catalyst is minimized.

As mentioned above, when the hydrogenation catalyst modified in accordance with the invention is used in a hydrogenation of a nitrile a surprisingly good selectivity in favor of the corresponding primary amine is achieved. In the present reaction, less byproducts, especially less secondary and tertiary amines, are produced as compared to when the corresponding unmodified hydrogenation catalyst is employed. The increase in selectivity is achieved with the activity of the hydrogenation catalyst remaining unchanged. Consequently, hydrogenation of nitrites can be carried out more efficiently.

A further advantage of the hydrogenation catalyst modified in accordance with the invention is that, after the modification it can be stored under water for a long time, i.e., for at least 30 days, without its activity and selectivity being lost. Therefore, the use of the modified catalyst in a hydrogenation need not be undertaken immediately after its modification.

Another process in accordance with the invention is the use of the hydrogenation catalyst modified in accordance with the invention to catalytically hydrogenate a nitrile to the corresponding primary amine. This process includes using as the hydrogenation catalyst one which has been obtained in accordance with the modification process defined above.

The hydrogenation catalyst modified in accordance with the invention which is to be used can be employed either after isolation from the mixture obtained after completion of the modification process or immediately and without isolation in this mixture.

To isolate it, the modified catalyst can be washed by sedimentation or filtration and suspension with fresh dispersion medium or rinsing of the filter cake. The same solvent can be used for the modification process as that which is usually used for the subsequent hydrogenation, so that in the second case an intermediary stage supplementation of the amount of solvent may be required. In this case, however, it is important that the modification agent is consumed, i.e. is no longer detectable, in order to avoid side reactions in the subsequent hydrogenation.

In principle, all nitrites can be hydrogenated selectively to their corresponding primary amines by the hydrogenation process in accordance with the invention. In particular, aliphatic nitrites, e.g. alkyl and alkenyl nitrites, aryl nitrites as well as heteroaryl nitrites may be hydrogenated. The term "aryl" as used herein embraces not only the usual unsubstituted aryl groups, i.e. phenyl and naphthyl, but also corresponding substituted phenyl and naphthyl groups as are illustrated in more detail above in connection with the definitions of $R^2$, $R^3$, and $R^4$. Likewise, the term "heteroaryl" means those groups which are illustrated in more detail above in connection with the definitions of $R^2$, $R^3$, and $R^4$.

With the exception of the use in accordance with the invention of the modified hydrogenation catalyst, the hydrogenation process can be carried out under hydrogenation conditions which are known per se, especially with respect to solvent, temperature, pressure, amount of hydrogenation catalyst as well as duration of the hydrogenation reaction. However, in order to arrive as selectively as possible at the respective primary amine, the hydrogenation is preferably carried out in pure ammonia or in mixtures of ammonia and an organic solvent which are known per se for this purpose. Suitable organic solvents in such mixtures are those mentioned above in connection with the dispersion medium.

Also, the isolation and the purification of the respective hydrogenation product can be carried out according to methods known per se.

The following Examples are provided to further illustrate the processes in accordance with the invention. These Examples are illustrative only and are not intended to limit the scope of the invention in any way.

In the following examples, the concentration data refer to the weight of the respective hydrogenation catalyst modified in accordance with the invention and the selectivity refers to hydrogenations with 100% conversion with respect to the nitrile and possible intermediates which may result now and then during the reaction.

EXAMPLES

Example 1

Formaldehyde as the modification agent 40 g of pynitrile (4-amino-5-cyano-2-methypyrimidine) were hydrogenated in the presence of 5 g of commercially obtainable Raney nickel (Degussa-Hüls AG, Frankfurt-a-M, Germany; also the source of this catalyst in the subsequent Examples in which it is mentioned), 1.475 l of methanol and 300 g of ammonia at a temperature of 110° C. and 40 bar (4 MPa) overall pressure. After 5 hours a 96.4% yield of primary amine (4-amino-5-aminomethyl-2-methylpyrimidine) was achieved, with secondary amine also being produced in 1.9% yield.

When, prior to the hydrogenation, the Raney nickel (5 g) is stirred with 12 g of water and 0.36 g of 35% aqueous formaldehyde solution (% by weight) for 30 minutes at room temperature (25° C.) under nitrogen or argon, thereafter decanted off and rinsed three times with 50 ml of deionized water each time, a selectivity of 99.6% (secondary amine content <0.1%) is achieved after 5 hours using the thus-modified catalyst. When the modified catalyst is employed for the first time after storage under water for 30 days, a selectivity of 99.7% (secondary amine content <0.1%) is achieved.

Example 2

Carbon monoxide as the modification agent 40 g of pynitrile were hydrogenated in the presence of 5 g of commercially obtainable Raney nickel, 1.475 l of methanol, and 300 g of ammonia at a temperature of 110° C. and 40 bar (4 MPa) overall pressure. After 5 hours a 96.4% yield of primary amine was achieved, with secondary amine also being produced in 1.9% yield.

When, prior to the hydrogenation, the Raney nickel (5 g) is stirred with 12 g of water and 50 ml of carbon monoxide for one hour at room temperature (25° C.) under nitrogen or argon, thereafter decanted off and rinsed three times with 50 ml of deionized water each time, a selectivity of 98.8% (secondary amine content <0.1%) is achieved after 5 hours using the thus-modified catalyst.

Example 3

Acetaldehyde as the Modification Agent 40 g of pynitrile were hydrogenated in the presence of 6 g of commercially obtainable Raney nickel, 1.475 l of methanol, and 300 g of ammonia at a temperature of 110° C. and 40 bar (4 MPa) overall pressure. After 5 hours a 96.4% yield of primary amine was achieved, with secondary amine also being produced in 1.9% yield.

When, prior to the hydrogenation, the Raney nickel (6 g) is stirred with 15 g of water and 0.2 g of acetaldehyde for one hour at 60° C. under nitrogen or argon, thereafter decanted off and rinsed three times with 50 ml of deionized water each time, a selectivity of 97.3% (secondary amine content <0.1%) is achieved after 5 hours using the thus-modified catalyst.

Example 4

Formaldehyde as the modification agent 40 g of pynitrile were hydrogenated in the presence of 10 g of commercially obtainable Raney cobalt (Degussa-Hüls AG, Frankfurt-a-M, Germany), 1.475 l of methanol, and 300 g of ammonia at a temperature of 110° C. and 40 bar (4 MPa) overall pressure. After 5 hours a 96.8% yield of primary amine was achieved, with secondary amine also being produced in 2.2% yield.

When, prior to the hydrogenation, the Raney cobalt (10 g) is stirred with 24 g of water and 0.72 g of 35% formaldehyde solution for one hour at room temperature (25° C.) under nitrogen or argon, thereafter decanted off and rinsed three times with 50 ml of deionized water each time, a selectivity of 99.1% (secondary amine content <0.1%) is achieved after 5 hours using the thus-modified catalyst.

Example 5

Formaldehyde as the modification agent 40 g of pynitrile were hydrogenated in the presence of 8 g of commercially obtainable nickel-on-silica (Degussa-Hüls AG, Frankfurt-a-M, Germany), 1.475 l of methanol, and 300 g of ammonia at a temperature of 110° C. and 40 bar (4 MPa) overall pressure. After 5 hours a 96.8% yield of primary amine was achieved, with secondary amine also being produced in 1.9% yield.

When, prior to the hydrogenation, the nickel-on-silica (8 g) is stirred with 20 g of water and 0.57 g of 35% formaldehyde solution for one hour at room temperature (25° C.) under nitrogen or argon, thereafter decanted off and rinsed three times with 50 ml of deionized water each time, a selectivity of 98.1% (secondary amine content <0.1%) is achieved after 5 hours using the thus-modified catalyst.

Example 6

Formaldehyde as the modification agent 100 g of benzonitrile were hydrogenated in the presence of 5.7 g of commercially obtainable Raney nickel and 2 l of methanol at a temperature of 100° C. and 40 bar (4 MPa) overall pressure. After 3 hours a 70.0% yield of primary amine (benzylamine) was achieved, with dibenzylamine also being produced in 29.8% yield.

When, prior to the hydrogenation, the Raney nickel (5.7 g) is stirred with 13.7 g of water and 0.41 g of 35% aqueous formaldehyde solution for one hour at room temperature (25° C.) under nitrogen or argon, thereafter decanted off and rinsed three times with 50 ml of deionized water each time, a selectivity of 83.6% (dibenzylamine content 12.6%) is achieved after 3 hours using the thus-modified catalyst.

Example 7

Formaldehyde as the modification agent 100 g of benzonitrile were hydrogenated in the presence of 5.7 g of commercially obtainable Raney nickel, 2 l of methanol, and 15 g of ammonia at a temperature of 100° C. and 40 bar (4 MPa) overall pressure. After 3 hours a 84.0% yield of primary amine (benzylamine) was achieved, with dibenzylamine also being produced in 15.4% yield.

When, prior to the hydrogenation, the Raney nickel (5.7 g) is stirred with 13.7 g of water and 0.41 g of 35% aqueous formaldehyde solution for one hour at room temperature (25° C.) under nitrogen or argon, thereafter decanted off and rinsed three times with 50 ml of deionized water each time, a selectivity of 94.1% (dibenzylamine content 5.3%) is achieved after 3 hours using the thus-modified catalyst.

Example 8

Formaldehyde as the modification agent 40.6 g of pyridine-3-carbonitrile were hydrogenated in the presence of 5.3 g of commercially obtainable Raney nickel, 2 l of methanol, and 31 g of ammonia at a temperature of 100° C. and 40 bar (4 MPa) overall pressure. After 5 hours a 78.1% yield of primary amine (3-aminomethyl-pyridine) was achieved, with secondary amine also being produced in 17.7% yield.

When, prior to the hydrogenation, the Raney nickel (5.3 g) is stirred with 12.7 g of water and 0.38 g of 35% aqueous formaldehyde solution for one hour at room temperature (25° C.) under nitrogen or argon, thereafter decanted off and rinsed three times with 50 ml of deionized water each time, a selectivity of 87.0% (dibenzylamine content 8.9%) is achieved after 3 hours using the thus-modified catalyst Example 9

Benzaldehyde as the modification agent 100 g of benzonitrile were hydrogenated in the presence of 5.7 g of commercially obtainable Raney nickel, 2 l of methanol, and 15 g of ammonia at a temperature of 100° C. and 40 bar (4 MPa) overall pressure. After 3 hours a 84.0% yield of primary amine (benzylamine) was achieved, with dibenzylamine also being produced in 15.4% yield.

When, prior to the hydrogenation, the Raney nickel (5.9 g) is stirred with 14.1 g of water and 0.37 g of benzaldehyde for one hour at room temperature (25° C.) under nitrogen or argon, thereafter decanted off and rinsed three times with 50 ml of deionized water each time, a selectivity of 94.2% (dibenzylamine content 4.8%) is achieved after 3 hours using the thus-modified catalyst.

Example 10

Carbon dioxide as the modification agent 100 g of benzonitrile were hydrogenated in the presence of 5.7 g of commercially obtainable Raney nickel, 2 l of methanol, and 15 g of ammonia at a temperature of 100° C. and 40 bar (4 MPa) overall pressure. After 3 hours a 84.0% yield of primary amine (benzylamine) was achieved, with dibenzylamine also being produced in 15.4% yield.

When, prior to the hydrogenation, the Raney nickel (6.0 g) is stirred with 15.0 g of water and 200 ml of carbon dioxide for one hour at room temperature (25° C.) under nitrogen or argon and thereafter decanted off and rinsed three times with 50 ml of deionized water each time, a selectivity of 91.8% (dibenzylamine content 8.1%) is achieved after 3 hours using the thus-modified catalyst.

Example 11

Formaldehyde as the modification agent 100 ml of valeronitrile were hydrogenated in the presence of 20 g of commercially obtainable Raney nickel, 2 l of methanol and 15 g of ammonia at a temperature of 120° C. and 20 bar (2 MPa) overall pressure. After 5 hours a 94.4% yield of primary amine (pentylamine) was achieved, with dipentylamine also being produced in 5.2% yield.

When, prior to the hydrogenation, the Raney nickel (21.9 g) is stirred with 37.5 g of water and 5.8 g of 35% formaldehyde solution for one hour at room temperature (25° C.) under nitrogen or argon, thereafter decanted off and rinsed three times with 50 ml of deionized water each time, a selectivity of 96.9% (dipentylamine content 3.2%) is achieved after 3 hours using the thus-modified catalyst.

Example 12

Acetone as the modification agent 40 g of pynitrile were hydrogenated in the presence of 6 g of commercially obtainable Raney nickel, 1.475 l of methanol, and 300 g of ammonia at a temperature of 110° C. and 40 bar (4 MPa) overall pressure. After 5 hours a 96.4% yield of primary amine was achieved, with secondary amine also being produced in 1.9% yield.

When, prior to the hydrogenation, the Raney nickel (6 g) is stirred with 14 g of water and 0.8 g of acetone for one hour under nitrogen or argon, thereafter decanted off and rinsed three times with 50 ml of deionized water each time, a selectivity of 97.6% (secondary amine content 1.6%) is achieved after 5 hours using the thus-modified catalyst.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for modifying a hydrogenation catalyst of a Raney nickel, Raney cobalt, nickel-on-carrier or cobalt-on-carrier type, comprising:
   a) providing a hydrogenation catalyst of the Raney nickel, Raney cobalt, nickel-on-carrier, or cobalt-on-carrier type; and
   b) treating the hydrogenation catalyst at temperatures of about 0° C. to about 120° C. with a modification agent selected from the group consisting of carbon dioxide, formaldehyde, a lower aliphatic aldehyde, an aromatic aldehyde, an aliphatic ketone, an aromatic ketone, a mixed aliphatic/aromatic ketone, glyoxal, pyruvaldehyde, and glyoxylic acid in a liquid dispersion medium consisting of water or an organic solvent for about 15 minutes to about 24 hours.

2. A process according to claim 1 wherein the modification agent is seiected from the group consisting of formaldehyde and a lower aliphatic aldehyde.

3. A process according to claim 2 wherein the lower aliphatic aldehyde is acetaldehyde.

4. A process according to claim 1 wherein the aromatic aldehyde is benzaldehyde or anisaldehyde.

5. A process according to claim 1 wherein the aliphatic, aromatic or mixed aliphatic/aromatic ketone is acetone.

6. A process according to claim 1 wherein the modification agent is formaldehyde.

7. A process according to claim 1 wherein the organic solvent is selected from the group consisting of an aliphatic hydrocarbon, an aromatic hydrocarbon, an alkanol, an aliphatic or cyclic ether, and a heteroaromatic.

8. A process according to claim 7 wherein the organic solvent is selected from the group consisting of pentane, hexane, benzene, toluene, methanol, ethanol, propanol, diethyl ether, tetrahydrofuran, dioxan, and pyridine.

9. A process according to claim 1 wherein the amount of modification agent used to treat the hydrogenation catalyst is about 1–30 wt. %, based on the amount of hydrogenation catalyst employed, when the modification agent is carbon dioxide.

10. A process according to claim 9 wherein the amount of modification agent is about 5–15 wt. %.

11. A process according to claim 1 wherein the amount of modification agent used to treat the hydrogenation catalyst is about 0.25–50 wt. %, based on the amount of hydrogenation catalyst employed, when the modification agent is selected from the group consisting of formaldehyde, a lower aliphatic aldehyde, an aromatic aldehyde, glyoxal, pyruvaldehyde, and glyoxylic acid.

12. A process according to claim 11 wherein the amount of modification agent is about 1–15 wt. %.

13. A process according to claim 1 wherein the amount of modification agent used to treat the hydrogenation catalyst is about 0.25–50 wt. %, based on the amount of hydrogenation catalyst employed, when the modification agent is an aliphatic, aromatic, or mixed aliphatic/aromatic ketone.

14. A process according to claim 13 wherein the amount of modification agent is about 5–20 wt. %.

15. A process according to claim 1 comprising carrying out the process at room temperature.

16. A process for the catalytic hydrogenation of a nitrile to a corresponding primary amine, comprising:

a) providing a modified hydrogenation catalyst formed by treating a hydrogenation catalyst selected from the group consisting of a Raney nickel, Raney cobalt, nickel-on-carrier, and cobalt-on-carrier type catalyst at temperatures of about 0° C. to about 120° C. with a modification agent selected from the group consisting of carbon dioxide, formaldehyde, a lower aliphatic aldehyde, an aromatic aldehyde, an aliphatic ketone, an aromatic ketone, a mixed aliphatic/aromatic ketone, glyoxal, pyruvaldehyde, and glyoxylic acid in a liquid dispersion medium consisting of water or an organic solvent for a duration of about 15 minutes to about 24 hours; and b) contacting a nitrile with the modified hydrogenation catalyst to catalyze the reaction of the nitrile to its corresponding primary amine.

17. A process according to claim 16 wherein the nitrile is selected from the group consisting of an aliphatic nitrile, an aryl nitrile, and an heteroaryl nitrile.

18. A process according to claim 17 wherein the nitrile is an alkyl nitrile or an alkenyl nitrile.

19. A process according to claim 16 further comprising isolating the primary amine from the reaction mixture.

* * * * *

UNITED STATES PATENT AND TRADEMARK OFFICE
CERTIFICATE OF CORRECTION

PATENT NO.      : 6,521,564 B2
DATED           : February 18, 2003
INVENTOR(S)     : Oliver Gerald Degischer and Felix Roessler It is certified that error appears in the above-identified patent and that said Letters Patent is hereby corrected as shown below:

<u>Column 8,</u>
Line 50, please change "seiected" to -- selected --.

Signed and Sealed this

Eighth Day of July, 2003

JAMES E. ROGAN
*Director of the United States Patent and Trademark Office*